US010561576B2

(12) United States Patent
Glenn et al.

(10) Patent No.: US 10,561,576 B2
(45) Date of Patent: Feb. 18, 2020

(54) INNOVATIONS IN MECHANICAL VENTILATORS

(71) Applicants: Fernandes Glenn, Thane (IN); Parikh Sarita, Mumbai (IN)

(72) Inventors: Fernandes Glenn, Thane (IN); Parikh Sarita, Mumbai (IN)

(*) Notice: Subject to any disclaimer, the term of this patent is extended or adjusted under 35 U.S.C. 154(b) by 233 days.

(21) Appl. No.: 15/529,522

(22) PCT Filed: Dec. 21, 2015

(86) PCT No.: PCT/IN2015/000450
§ 371 (c)(1),
(2) Date: May 25, 2017

(87) PCT Pub. No.: WO2016/103275
PCT Pub. Date: Jun. 30, 2016

(65) Prior Publication Data
US 2017/0304147 A1    Oct. 26, 2017

(30) Foreign Application Priority Data

Dec. 26, 2014    (IN) .......................... 4168/MUM/2014

(51) Int. Cl.
*A61H 31/02*    (2006.01)
*A61M 16/00*    (2006.01)
(Continued)

(52) U.S. Cl.
CPC .............. *A61H 31/02* (2013.01); *A61H 35/04* (2013.01); *A61M 16/0003* (2014.02); *A61M 16/0057* (2013.01); *A61M 16/024* (2017.08); *A61M 16/04* (2013.01); *A61M 16/10* (2013.01); *A61M 16/202* (2014.02); *A61H 2201/0157* (2013.01); *A61H 2201/0184* (2013.01);
(Continued)

(58) Field of Classification Search
CPC . A61H 31/02; A61H 2031/025; A61M 16/00; A61M 16/003; A61M 16/024; A61M 16/0057
USPC .......................................................... 601/152
See application file for complete search history.

(56) References Cited

U.S. PATENT DOCUMENTS

4,676,232 A * 6/1987 Olsson ................. A61H 9/0078
601/106
4,815,452 A * 3/1989 Hayek .................... A61H 31/02
128/205.26
(Continued)

*Primary Examiner* — Kristen Matter (57) ABSTRACT

A respiratory device of negative pressure type comprising a shell fastened to the user's chest and/or abdomen with minimal dead space, one or more vacuum and compressed air chambers attached to the shell; vacuum generating and compressed air generating sources connected to the vacuum and compressed air chambers respectively, one or more openings on the shell to allow exchange of the air enclosed between shell and user's body, with the vacuum and compressed air chambers; a valve shuttling between the vacuum and compressed air chambers. By having low dead space, pre-generated vacuum and compressed air close to the user, and the use of fast acting valves in some embodiments, the power requirement, weight, and size are reduced, making the device low cost and portable. In some embodiments, the vacuum and compressed air generating sources can be mounted on the shell itself, making the device ambulatory.

11 Claims, 3 Drawing Sheets

(51) Int. Cl.

| | | |
|---|---|---|
| *A61M 16/20* | (2006.01) | |
| *A63B 24/00* | (2006.01) | |
| *A61M 16/04* | (2006.01) | |
| *A61M 16/10* | (2006.01) | |
| *A61H 35/04* | (2006.01) | |
| *A61M 16/16* | (2006.01) | |
| *A61M 11/06* | (2006.01) | |
| *A63B 23/18* | (2006.01) | |
| *A63B 21/00* | (2006.01) | |
| *A63B 21/008* | (2006.01) | |
| *A63B 71/00* | (2006.01) | |
| *A63B 71/06* | (2006.01) | |

(52) U.S. Cl.
CPC ......... *A61H 2201/165* (2013.01); *A61H 2201/1619* (2013.01); *A61H 2201/5015* (2013.01); *A61H 2201/5071* (2013.01); *A61H 2201/5082* (2013.01); *A61H 2201/5089* (2013.01); *A61H 2201/5097* (2013.01); *A61H 2230/405* (2013.01); *A61M 11/06* (2013.01); *A61M 16/0063* (2014.02); *A61M 16/16* (2013.01); *A61M 2016/0015* (2013.01); *A61M 2016/0027* (2013.01); *A61M 2205/3331* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2205/8212* (2013.01); *A61M 2209/088* (2013.01); *A61M 2230/205* (2013.01); *A61M 2230/50* (2013.01); *A63B 21/0085* (2013.01); *A63B 21/4007* (2015.10); *A63B 23/18* (2013.01); *A63B 24/0087* (2013.01); *A63B 71/0009* (2013.01); *A63B 2024/0093* (2013.01); *A63B 2071/0627* (2013.01); *A63B 2220/56* (2013.01); *A63B 2225/20* (2013.01); *A63B 2225/50* (2013.01); *A63B 2230/425* (2013.01); *A63B 2230/438* (2013.01); *A63B 2230/505* (2013.01)

(56) References Cited

U.S. PATENT DOCUMENTS

| | | | | |
|---|---|---|---|---|
| 4,971,042 | A * | 11/1990 | Lerman | A61H 31/00 601/44 |
| 5,076,259 | A * | 12/1991 | Hayek | A61H 31/02 601/44 |
| 5,343,878 | A * | 9/1994 | Scarberry | A61H 31/02 128/200.24 |
| 7,785,280 | B2 * | 8/2010 | Kivisto | A61H 9/0078 601/148 |

* cited by examiner

INNOVATIONS IN MECHANICAL VENTILATORS

CROSS-REFERENCE TO RELATED APPLICATIONS

This application claims the benefit of PCT Application No. PCT/IN2015/000450 filed on Dec. 26, 2015.

FIELD OF INVENTION

Embodiments of the present invention relate to the field of mechanical ventilators, and more particularly, to the field of portable and ambulatory medical ventilators, of the negative pressure ventilator type, that mimic the natural breathing process.

BACKGROUND OF INVENTION

Respiratory illness is a major killer worldwide, consistently featuring in the top 10 leading causes of death as per the World Health Organisation (WHO). The problem is worse in developing countries such as India, where respiratory illness as the $2^{nd}$ largest killer. Ventilators are used to provide crucial, life-saving respiratory support in case of respiratory distress and failure. These are used not only for respiratory illness, but also in other medical scenarios, such as post-cardiac surgery and so on, to reduce respiratory effort and divert the patient's resources to other critical organs.

However conventional ventilators are very expensive, often-times invasive and require highly skilled staff to operate them. Ventilator support is thus short in supply, especially in poorer, developing countries, thereby depriving many, especially from the poorer sections of society, from receiving crucial life-saving respiratory support in medical emergencies.

Further, conventional ventilators are generally the positive-pressure types, which force air at higher than atmospheric pressures into the lungs. These ventilators are known to cause further medical complications and even death, for example, volutrauma and barotrauma due to high pressures, and infection and pneumonia due to the invasive and forceful nature of these devices. There is in fact a distinct class of medical injuries called "Ventilator Induced Lung Injury" (VILI).

As a result of these dangerous "side-effects" conventional positive-pressure ventilators are especially not suitable for new-born infants, especially premature infants, who often need initial respiratory support to survive. In preterm infants, the high pressures used in these devices cause broncho-pulmonary dysplasia or chronic lung disease of the newborn or cognitive impairment, causing severe disability for life. In fact, in infants less than 1 kg weight, they are considered to be "not cost-effective" and thus many a precious life is lost.

Negative pressure ventilators are also present in the prior art, in fact these were the first type of ventilators to be developed, and were the only types that were life-saving during the polio epidemic of the 1950s. The traditional types encase the entire body in a tank and reduce the pressure in tank, resulting in a negative pressure around lungs, which causes air to move via the nostrils into the lungs gently, at atmospheric pressure, to equalize the pressure. They thus mimic the natural breathing process, where movement of the respiratory muscles creates negative pressure in the lungs, and ambient air moves in through the nostrils to equalize the pressure.

Although highly effective, negative pressure ventilators still have several drawbacks. E.g. the neck seal can cause cerebral hemorrhage and neck soreness. Patient care also becomes difficult, as the entire body was enclosed in a tank. Also, since the entire body is enclosed in a negative pressure chamber, venous return to heart is impeded.

Cuirass type negative pressure ventilators, which enclose the chest and abdomen of the user, are an improvement which eliminates the above drawbacks of traditional negative pressure ventilators, but these also have a number of limitations. The cuirass is large, unwieldy, to fit differently sized users and are connected with long, large bore pipe to a large vacuum pump, which generates the required negative pressure in the cuirass. The vacuum pump needs to be large as there is a lot of dead space within the cuirass and the wide bore pipe, which has to be evacuated and also because it needs to quickly generate the required negative pressure. Due to this large size of the vacuum pump, the device consumes high power, is very noisy, heavy and expensive. It thus cannot be used in poorer areas, and in areas with low, unstable or no electric supply, such as rural villages.

Further, cuirass ventilators, though portable, are not ambulatory, due to the cumbersome wide bore pipe connected to the large and heavy vacuum pump.

e.g. People suffering from chronic respiratory illness such as asthma, or chronic bronchitis (which affect a large number of children and adults worldwide), need ventilator support in their daily lives, due to exhaustion of respiratory muscles. However, they are unable to move about freely, due to the attached tube and heavy vacuum pump, thereby severely restricting their activities, productivity and quality of life.

There is thus a grave need worldwide for a ventilator device that is ambulatory, safe, low-cost, low-power as well as easy-to-use while having all advanced functionality of conventional ventilators, like customizable settings for users, safety alarms, additional sensors, nebulization, humidification etc. and which can thus provide life-saving and life-enhancing respiratory support to people of all economic backgrounds, without disrupting their daily lives, in a safe manner.

SUMMARY OF INVENTION

Embodiments of the present invention relate to low cost, low power, portable and ambulatory negative-pressure respiratory device comprising: a shell enclosing the front and side parts of chest and/or abdomen of the user, one or more vacuum chambers attached to shell, one or more compressed air chambers attached to shell, a vacuum generating source connected to the said one or more vacuum chambers, a compressed air generating source connected to the one or more compressed air chambers, one or more openings on the shell to allow exchange of the air which is enclosed between shell and user's body with the vacuum and compressed air chambers, a valve shuttling between vacuum and compressed air chambers, one or more sensors and one or more electronic control unit attached to the shell to operate the valve and/or the vacuum and compressed air generating sources and/or any other electronic component of the said device, one or more battery and/or electrical connection to the mains or an external power source attached to electronic control unit, to power the device, a soft, comfortable sealing mechanism to seal the shell to the user's body and a shell fastening mechanism to fasten the shell to the user's body.

The device is non-invasive and mimics the natural breathing process, requiring no training for use. The device is strapped onto the user and settings are configurable even remotely, or else the device can function in default mode in some embodiments, generating the required respiratory rhythm, rate and volume based on the size of the shell selected.

At initiation of inhalation by user, or based on pre-defined time settings programmed in the electronic control unit, the valve opens the vacuum chamber and starts evacuating air between the shell and the user's body, creating a negative pressure around the user's lungs, initiating and causing inhalation. At the end of inhalation, the valve closes the vacuum chamber and opens the compressed air chamber and starts filling in air between the shell and user's body, initiating and aiding exhalation. Thus, this device aids both phases of the respiratory cycle.

The vacuum and compressed air generating sources pre-evacuate the vacuum chamber and pre-fill the compressed air chambers respectively, which, along with the fast acting valve of some embodiments allows for ultrafast initiation of both cycles of respiration. This allows for very good synchronizing with the user's respiratory effort, reducing greatly the user's effort for both—inhalation and exhalation. Further, by being fast acting, the device also reduces the negative pressure needed to be generated around the lungs, to cause the desired amount of air to enter the lungs on inhalation. This results in gentle respiration, and is thus extremely safe. This also reduces the power requirement of the vacuum generating source, and thus the size and weight of the device.

To reduce the power requirement for this device, the present invention utilizes several methods.

Firstly, having pre-generated vacuum and compressed air stored in vacuum and compressed air chambers attached to the device, communicating with it via openings on the shell allows for smaller and lower power vacuum generating and compressed air generating sources. As the vacuum and compressed air is pre-generated, the vacuum generating and compressed air generating sources have a lighter load and thus do not have to be very powerful to achieve the desired vacuum or compression instantly on valve opening. This enables them to be much smaller and lower power, compared to the prior art.

Secondly, the power and size reduction is achieved by reducing the dead space between user's body and the vacuum generating source. This is done in two ways. In some embodiments, this is done by having many sized shells to choose from, enabling the user to obtain a well-fitting shell with minimal dead space and/or by making the shells slightly flexible, yet structurally capable of taking the vacuum and compressed air, allowing for minimum dead space.

The other way is that unlike the prior art, there is no wide bore tube connecting the shell to the vacuum generating source, further reducing the volume of dead space to be evacuated from inside the wide bore tube. These two ways reduce the amount of air that needs to be evacuated to generate the desired negative pressure in the lungs, reducing the size and weight of vacuum and compressed air generating sources required and thus, the power requirement.

Thirdly, some embodiments have an ultrafast acting valve, in microseconds. This requires less negative pressure to be generated by the vacuum pump, to make the desired volume of air enter the user's lungs on inhalation. This is again different from all prior art which utilizes valves operating in milliseconds, and hence all prior art has a higher power requirement to achieve same volume of air in the lungs on inhalation.

Another advantage of the ultrafast opening valve and pre-generated vacuum of some embodiments is that they also reduce the chance of nasal occlusion in case of users with bulbar paralysis (certain paralysis affecting muscles of nose and upper respiratory tract). In such users, if the negative pressure takes time to build up, much more negative pressure is needed than if it is generated quickly. At higher negative pressures, there are chances that the upper respiratory tract in such users can collapse, blocking the airflow into the lungs. All valves and pumps in the prior art operate in milliseconds, but by having pre-stored vacuum and a valve that acts in microseconds, the negative pressures generated by this device are very low and this does not cause collapse of the nasal tract in such users, making it suitable for use even in such users.

All of the above allow for lower power and thus small pumps to be utilized in this invention, allowing the vacuum and compressed air sources to even be mounted on the shell, unlike the prior art, making the device ambulatory. This feature also allows this device to be used during transport of users from remote areas to hospitals on stretchers and local transport. Smaller sized vacuum pump and compressors, with reduced power requirement, also reduce the cost of the device.

Further, the shell of this device is not cumbersome. Unlike prior art, it is lightweight and small in size, and in some embodiments could even start automatically on fastening, making it very easy to use.

Thus the present invention is low cost, lightweight, ambulatory, portable, safe and easy to use.

Some embodiments also have a provision to utilize exhaust from the device to provide warm humidified and/or nebulized air to the patient with negligible additional energy cost.

The principal object of this invention is to provide a safe, low cost, lightweight, low power, respiratory device that can be operated without any skilled operator.

Another object of this invention is to make the device ambulatory to enable users to perform daily activities and lead quality, productive lives, while on respiratory support.

Another object of this invention is to make the ventilator shells such that several sizes can be made economically, such that shells fit the users comfortably, with minimum dead space per user.

Another object of this invention is to make the ventilator shells lightweight and flexible yet capable of withstanding the vacuum and compressed air between the shell and user's body, allowing for a better, more comfortable fit and reducing leakage Another object of this invention is to reduce user effort, by providing instantaneous synchronization with user's respiratory effort, which is achieved with sensors and fast acting valve in microseconds.

Another object of this invention is to seal the device well to the user's body to minimize user discomfort, while at the same time preventing leakage.

Another object of this invention is to make a respiratory device that auto-starts with the minimum mandatory breaths, to prevent any inadvertent loss of life due to losing critical minutes setting up the device, with the ability to be customized for the user even later, after the first few critical care steps have been initiated.

Another object of this invention is to make the device economical for hospitals or health care centers already having vacuum and compressed air outlets.

Another object of this invention is to make the device lighter for bedridden users and requiring low power, even if connected to an external vacuum and/or compressed air generating sources.

Another object of this invention is to be able to generate vacuum and compressed air even with just a compressor alone.

Another object of this invention is to be able to provide nebulized medicine and/or warm humidified air as and when required to the user with negligible or no additional energy cost.

Another object of this invention is to be able to provide a device that can provide respiratory training, especially useful for athletes, for those with chronic respiratory disease, as well as for those with stress induced illnesses.

Another object of this invention is to be able to provide a low cost, low power, portable, ambulatory, lightweight positive pressure ventilator.

While the invention is described herein by way of example using several embodiments and illustrative drawings, those skilled in the art will recognize that the invention is not limited to the embodiments of drawing or drawings described, and are not intended to represent the scale of the various components. Further, some components that may form a part of the invention may not be illustrated in certain figures, for ease of illustration, and such omissions do not limit the embodiments outlined in any way. It should be understood that the drawings and detailed description thereto are not intended to limit the invention to the particular form disclosed, but on the contrary, the invention is to cover all modification, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to. Further, the words "a" or "an" mean "at least one" and the word "plurality" means one or more, unless otherwise mentioned.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

These and other features, benefits and advantages of the present invention will become apparent by reference to the following text figures, with like reference numbers referring to like structures across the views, wherein.

DETAILED DESCRIPTION OF THE INVENTION

The respiratory device disclosed in the present invention simulates the natural breathing process. To initiate a breath, it creates a negative pressure around the chest cavity either directly (if the ventilator shell is attached to chest) or indirectly (if the ventilator shell is attached to the abdomen, in which case expansion of the abdomen lowers the diaphragm, indirectly leading to negative pressure in the lungs)—leading to air entering into the lungs via the nostrils, to equalize the pressure, and thus causing inspiration. When the pressure is equalized, the device now aids the natural elastic recoil of the lungs by pushing in compressed air around the chest cavity or abdomen—helps expel air from the lungs, thus aiding exhalation.

Figure 1:
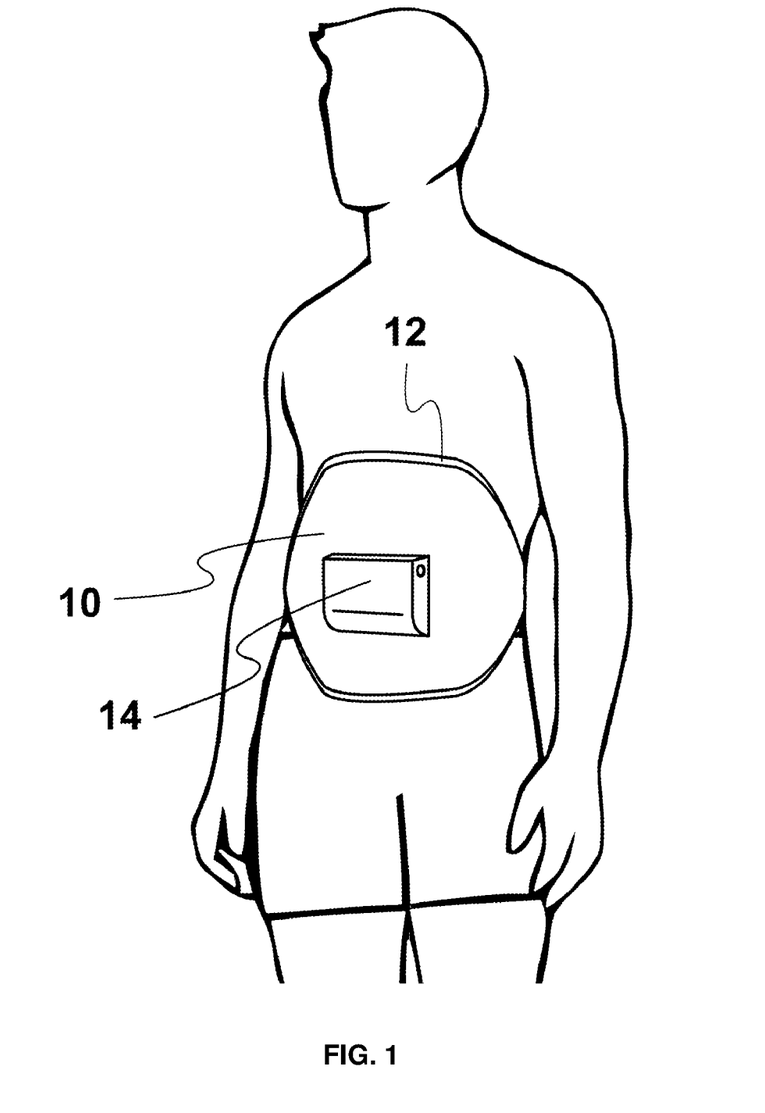
FIG. 1 illustrates an outline view of the respiratory device according to one embodiment of the present invention, fastened on a user.
Figure 2:
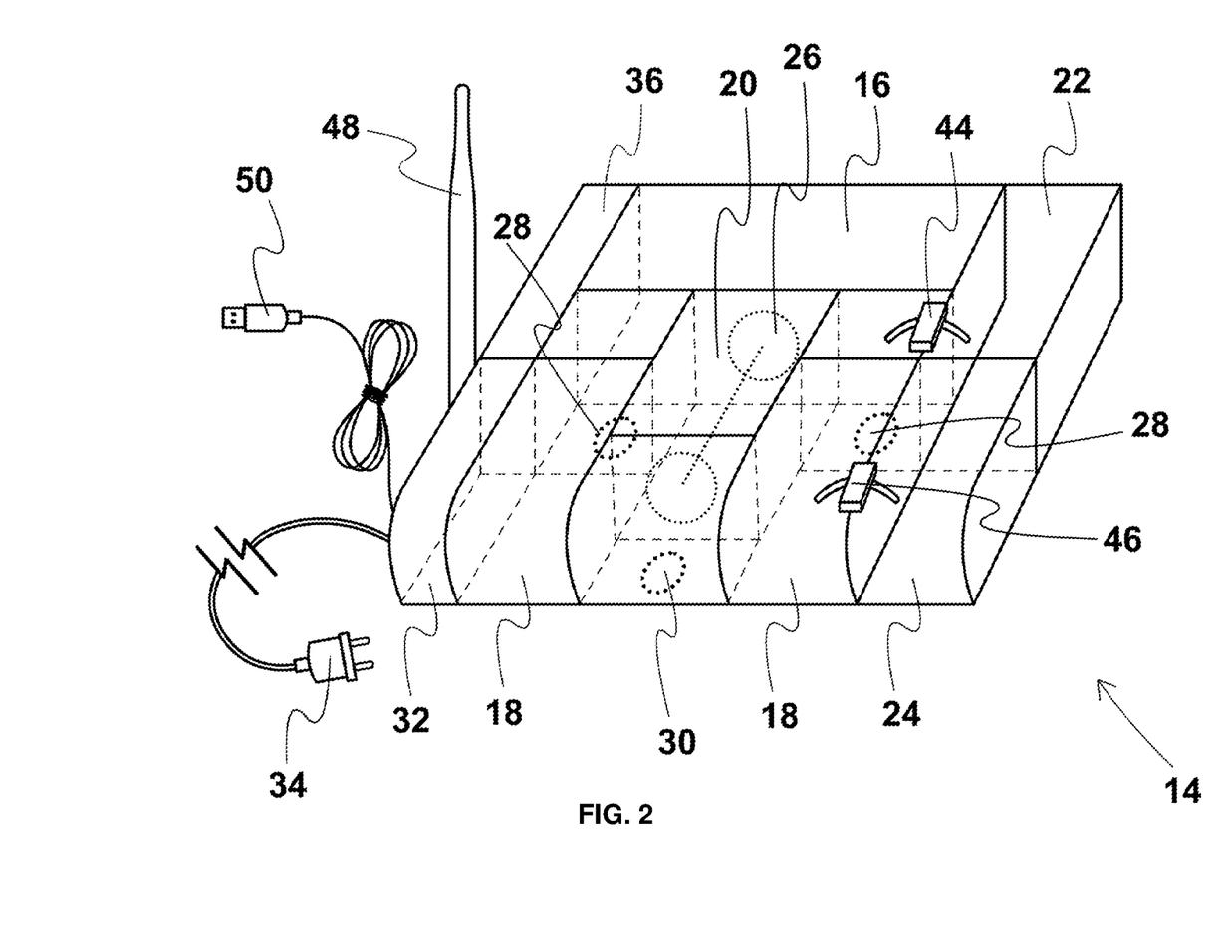
FIG. 2 illustrates a perspective view of the assembly of the respiratory device according to one embodiment of the present invention.

FIGS. 1 and 2 illustrate the respiratory device according to one embodiment of the present invention, which is the best mode or preferred embodiment. FIG. 1 shows shell 10 which encloses the front and side parts of the abdomen of the user, with seal 12 that seals the shell 10 and prevents leakage of air between the shell and user's body. The shell is fastened to the body of the user by means of a fastener. Fixed onto the shell 10 is assembly 14 which is attached to the shell 10, which comprises other parts of the device as detailed in FIG. 2. Assembly 14 comprises vacuum chamber 16 and 2 compressed air chambers 18, valve housing 20, vacuum generating source which is a vacuum pump 22 and a compressed air generating source which is a compressor 24, connected to vacuum chamber 16 and compressed air chambers 18 respectively. Valve 26, located inside valve housing 20 communicates with vacuum chamber 16 and with compressed air chamber 18. Valve housing 20 communicates with shell 10 via openings 28 and 30. Also mounted on the shell 10 is electronic control unit 32, with electrical connection 34 and battery 36. Pressure sensors are present in vacuum chamber 16, compressed air chamber 18 and between shell 10 and user's body. Pressure and/or flow regulators 44, 46 are situated between vacuum pump 22 and vacuum chamber 16 and between compressor 24 and compressed air chamber 18 respectively. The device can be programmed via wired and/or wireless connections connected to the electronic control unit 32, which in this embodiment are Wifi module 48 and USB cable 50 respectively. One or more breath sensors are situated in one or more openings in the shell.

Initiation of the user's inhalation is sensed by the breath sensor. This leads to synchronous opening of the vacuum chamber 16 by the fast acting valve 26. The vacuum chamber 16 has vacuum pre-generated by the vacuum pump 22 and the air inside the shell 10 now enters into the vacuum chamber 16 via openings 28 on the shell 10. This instantly reduces pressure around the user's abdomen, initiating expansion of the abdomen into the negative pressure area. This leads to contraction of the diaphragm and thus the simultaneous expansion of the lungs, initiating inhalation of air via the nostrils into the lungs. This simulates natural respiration, wherein expansion of the lungs by the respiratory muscles causes negative pressure in the lungs, causing atmospheric air to enter the lungs via the nostrils. Since the valve 26 acts within microseconds, and also since there is pre-generated vacuum stored in the vacuum chamber 16 by vacuum pump 22, the vacuum generation is instantaneous. This reduces user respiratory effort, thereby increasing user ease and very importantly, allowing the ailing user's energy resources to be utilized for other vital body functions. This device can be thus advantageously utilized by any critically ill user, even one who does not require respiratory support, to reduce the physical effort of the user.

Additionally, the valve 26 could also open the vacuum chamber 16 based on preset timing programmed on the electronic control unit 32.

The vacuum chamber 16 could be sized to evacuate the entire tidal volume (volume of air taken in and expired per breath, which is 7 ml/kg of body weight) at once, or it could be smaller and the vacuum generated in it could be regulated by the pressure and/or flow regulator 44 to continuously evacuate the air enclosed between the shell 10 and the user's body over 1-2 seconds, such that the desired tidal volume is evacuated over this period of 1-2 seconds or in any desired time. The latter mode is preferred as it needs a smaller chamber and causes smoother, non-jerky expansion of abdomen and chest.

Pressure sensor inside vacuum chamber 16 and pressure sensor between the user's body and shell 10 provide feedback control to the vacuum pump 22 and the pressure and/or flow regulator 44 that is regulating the pressure and/or controlling the flow, to maintain appropriate vacuum in the vacuum chamber 16 to efficiently evacuate the air between the shell 10 and the user's body, such that the desired tidal volume is evacuated per breath.

In another embodiment, the vacuum pump 22 and compressor 24 could be directly motor controlled based on feedback from the sensors.

Once the desired tidal volume is evacuated, the further evacuation of the air between shell 10 and the user's body is stopped, inhalation may be held for desired time if any, and then the valve 26 shuts the vacuum chamber 16, simultaneously opening compressed air chamber 18. Air from compressed air chambers 18 enters the gap between shell 10 and the user's body via opening 30 on the shell 10. This air actively pushes the abdomen, aiding the natural deflation of the abdomen that would happen during exhalation due to elastic spring recoil of the lungs. This is especially helpful in people with chronic lung diseases like asthma and chronic bronchitis, who have trouble exhaling completely. The amount and pressure of compressed air in compressed air chamber 18 is regulated by the pressure and/or flow regulator 46 based on feedback from pressure sensor between the user's body and the shell 10, and the pressure sensor in compressed air chamber 18.

All the sensors, the regulators 44, 46, the vacuum pump 22 and the compressor 24 are controlled by electronic control unit 32, which coordinates the action of all the components, to achieve the desired pressures, flow rates, tidal volumes, breath rates and respiratory rhythms. Some of these settings can be pre-programmed onto the control unit 32, while others could be programmed later at any time, via wifi module 48 or USB cable 50, which would connect to a suitable computing device or mobile phone. In other embodiments the same can be done via any other suitable wired or wireless means and even via the internet. This allows for a much lighter and economical device. In yet another embodiment, the respiratory device can have a keypad and LCD, or a touchscreen, or any other suitable input and/or display device attached to it, to directly program the device.

In other embodiments, other sensors such as temperature sensor, oxygen saturation sensor, and so on could also be used to further fine-tune the ventilator support given to the user, by altering the tidal volumes, rate or rhythm as needed.

The user data gathered from the sensors could be stored on the device or transmitted to any external device. All of the aforesaid are powered by battery 36 and can also be powered by the mains via electrical connection 34. The battery 36 is ideally one or more mobile phone batteries, which are readily available, chargeable and replaceable. The user can be completely mobile with the said embodiment, running on lightweight battery when the user is mobile, and charging the one or more batteries via electrical connection 34 when resting. Electrical connection 34 could also directly power the device.

Soft seal 12 between the shell 10 and the user's body, prevents leakage of air. The said seal 12 in the preferred embodiment is an open cell soft foam with a skin on the outside, preventing air from the seal from communicating with the atmosphere, while allowing movement of air within the seal, making it a very soft and comfortable and yet sturdy seal.

The shell 10 can be fabricated in several sizes and can even be custom-made. Further, the shells can be slightly flexible, allowing the ready sizes to be further adjusted, thus allowing the shell to closely fit the body of all users. This minimizes the dead space between the shell and the user's abdomen to around 1-2 liters, preferably around 1 liter.

Further in several embodiments, the shell 10 and the chambers 16, 18 are preferably made of thin walls that could be double walls with supporting fins or single walls supported by narrowly spaced ribbed structure, allowing for greater strength at lighter weight than the plain thick shells of the prior art that were needed to withstand the pressure and vacuum generated. This also makes the shells slightly flexible, allowing for a better, more comfortable fit with less dead space and reduced leakage.

The shell 10 is fastened to the user's body by means of an adjustable fastener. In the preferred embodiment, the respiratory device is configured to auto-start on locking the fastener, thus allowing immediate respiratory support which could be life-saving in many cases. The respiratory device in this case would auto-start with a default minimum respiratory breaths and tidal volume suitable for the said shell size. The respiratory device could then be set appropriately for the user at any later time.

Normal respiratory effort requires 2.5 watts of energy expenditure by a person. The smallest portable respirators have a power requirement of 50-100 watts. Whereas the present invention allows a much smaller vacuum pump 22, and compressor 24, and much lower power requirement, in the range of 5-20 watts, preferably 5-10 watts. This is achieved by using several methods.

Firstly, by having vacuum and compressed air chambers 16, 18 respectively attached to the shell 10. Their function is to pre-generate sufficient vacuum and compressed air to instantly evacuate and compress respectively on opening of valve 26. By having pre-stored vacuum and compressed air attached to the shell 10, the efficiency of the vacuum generation and compressed air generation is greatly improved, allowing for the use of low power, lightweight and small sized pumps, to provide desired vacuum and compression quickly, thus also allowing the vacuum and compressed air sources, vacuum pump 22 and compressor 24 respectively, to be mounted on the shell 10, compared to prior art.

This fast vacuum generation is aided by the fast acting valve 26, which also reduces the power required by the vacuum pump 22, as this instantaneous action requires much less negative pressure to be generated to allow inhalation of desired volume of air into the lungs.

Further, the dead space between the shell 10 and the user's body and also between the shell 10 and the vacuum pump 22 is greatly reduced. Prior art respiratory devices have very high dead space between the user's body and the shell, to accommodate for various patient sizes, and further dead space in the large bore tube used to connect the shell to the vacuum pump. Their vacuum pump too is large and heavy, to enable it to quickly evacuate this large dead space, to generate the desired negative pressure and cannot be mounted on the shell, thus making the prior art devices non-ambulatory.

Whereas in the present invention, the shell 10 is fabricated in several sizes to accommodate different users and is further slightly flexible and adjustable, thus minimizing the dead space between the shell and the user's abdomen. Also, there is no wide bore tube to be evacuated between the vacuum pump 22 and the shell 10. This reduces the power requirement of the vacuum pump 22, as it has to evacuate less air from this dead space to create enough negative pressure to start expansion of the lungs, and allows for a smaller size of vacuum pump 22 and compressor 24.

The entire respiratory device described above is lightweight and ideally weighs less than 1.5 kgs.

In another embodiment of the present invention, the vacuum and compressed air generating sources 22 and 24 respectively are external to the shell 10, and are connected to it by means of two small diameter (<1 cm) pipes. The said external sources could be external vacuum and compressor pumps or external vacuum and compressed air outlets respectively, of hospital lines. By having low dead space between the shell 10 and the user's body and by having compressed air chamber and vacuum chambers on the shell 10, the pipes connecting to these external sources can be of small diameter—less than 1 cm, ideally 5 mm, and preferably capable of withstanding 60 psi compressed air and 75% vacuum. Using such high pressure and vacuum, as are standard in hospital lines, further allows narrow bore tubes to generate the required pressure and vacuum, reducing dead space between the vacuum and compressed air sources, and the vacuum and compressed air chambers respectively. This embodiment is suitable in hospitals where compressed air and vacuum outlets are already available, reducing the cost of the device. Even in smaller nursing homes, such vacuum and compressed air lines can be specially installed, allowing for servicing of many users simultaneously on these respiratory devices, at a cheaper cost than that of a single conventional respirator. Such external sources could also provide a lightweight, cheaper, low power requiring ventilator support to bedridden users. Pressure and/or flow regulators on the pipes would have to be set to allow the desired vacuum or pressure in the vacuum and compressed air chamber respectively. Further, contrary to prior art devices, which are connected by wide bore tubes to vacuum pumps, this embodiment is still instantly acting due to pre-stored vacuum and compressed air in the vacuum and compressed air chambers, respectively, and can work with very narrow bore tubes, less than 1 cm, ideally around 5 mm.

In other embodiments of the present invention, the compressor performs both functions, compressing air into compressed air chamber and evacuating the vacuum chamber via venturi principle.

In other embodiments of the present invention, some or all parts of the assembly 14, are together on a separate piece attachable to the shell 10, allowing this separate piece to be used with different sized shells. Providing a large number of shells of different sizes makes it easy for users of different body sizes to obtain a shell that has minimum dead space in the preferred 1-2 liters range. Hospitals, schools, railways, etc. would have to stock up a large number of devices which would be costly. The shell 10 in this invention is preferably lightweight and economical, so that it can even be disposable. So by having some or all of the components of the assembly 14, which are most of the cost of the device, on a single separate unit, several shells can be used with one or a few such units and the cost drops drastically, since all shells are not being used at a time. This is also useful in case of growing children, who only need to change the shell 10 as they grow.

Another application of the device is in training the respiratory muscles of the user. This could be used even in individuals without respiratory illnesses, for various benefits. Resistance training could be provided by this device to the user's respiratory muscles, by suitably programming the said device such that the number of breaths are reduced, and the respiratory rhythm is improved. The device would not permit rapid, shallow, irregular breathing, for example, by applying appropriate resistance to the user's inhalation effort, or by helping the user perform a deep exhalation. Respiratory muscles undergoing such training, would be thus trained similar to resistance training of muscles of the arms or rest of the body.

Such muscles would require less energy for respiration, diverting that vital energy to other areas of the body, critical for both athletes and patients with chronic respiratory disease. It is also found that slower, deeper breaths are very calming and useful in reducing stress, and very healing in stress-caused illnesses like hypertension etc. As the ancient Sanskrit proverb states "For breath is life. If you breathe well, you will live long on earth." In fact, as stated by Dr. Arthur C. Guyton, MD, in "The Textbook on Medical Physiology", "All chronic pain, suffering and diseases are caused by a lack of oxygen at the cell level."

The present invention is thus very vital to city populations who suffer from the above in large numbers. Being portable, non-invasive, easy to use, safe and economical, it could be an important health promoting and disease preventive device.

Embodiments of this device could also be used to provide positive pressure ventilation. At certain times, e.g. during thoracic or abdominal or back surgeries, it is not possible to use this device in its negative pressure mode. In such and other similar occasions, this same device can also be used as a positive pressure device. The compressed air source 24 would filled in compressed air in the compressed air chamber 18 and the fast acting valve 26 and the pressure and/or flow regulator 46 would help pump air at the desired positive pressure into the user's lungs. During such use, the shell 10 need not be fixed to the user's chest and/or abdomen, and could be lying close to the user.

Other embodiments could utilize the compressed air chamber 18, the fast acting valve 26, and a compressed air source 24, with required sensors, control electronics, nasal pipe and/or mask and/or helmet and/or endotracheal tube etc. to provide positive pressure ventilation to the user, eliminating the vacuum chamber 16, vacuum generating source 22 and shell 10. This device could be strapped onto the patient by any suitable means, or placed close to the patient. This embodiment also has the advantage of fast acting valve 26 and pre-stored compressed air and thus would require less power, is lighter weight, and economical compared to conventional positive pressure ventilators.

Figure 3:
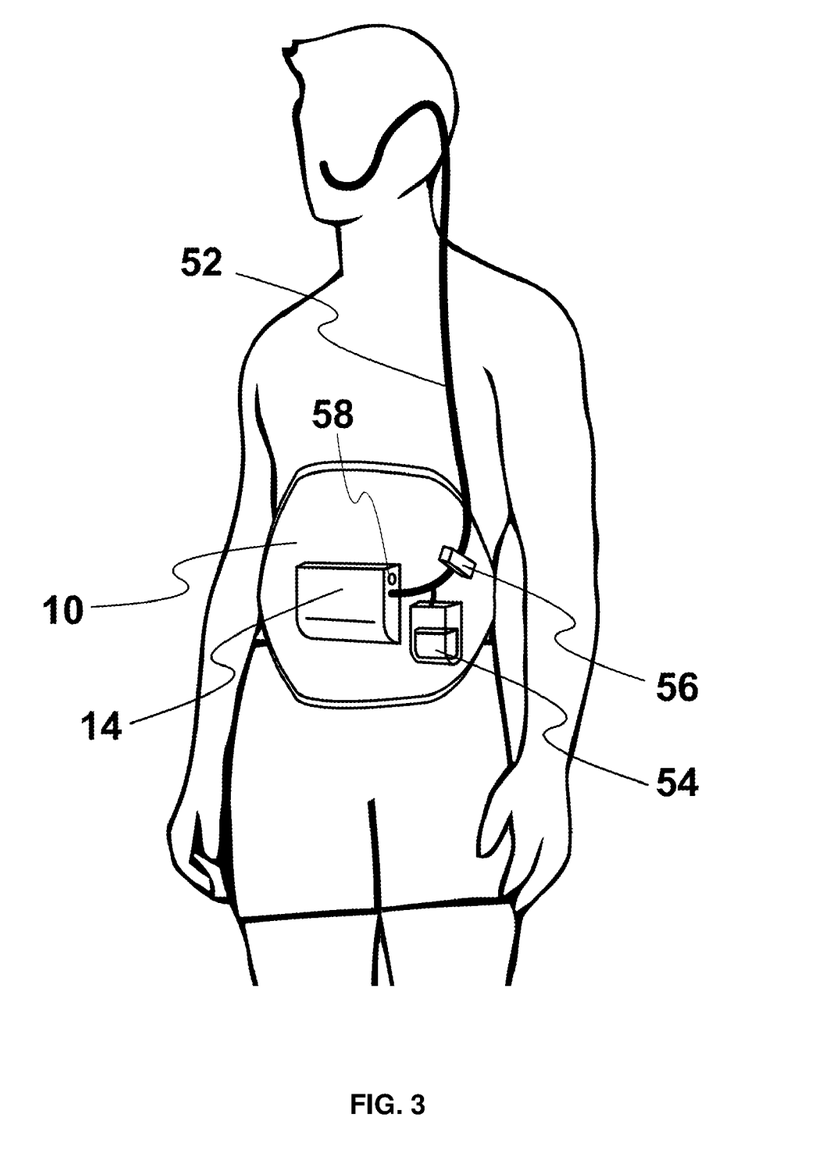
FIG. 3 illustrates an outline view of a respiratory device according to one embodiment of the present invention, wherein warm air from the vacuum pump exhaust is used to nebulise medication and/or to humidify air and deliver it to the user's nostrils.

FIG. 3 illustrates an outline view of a respiratory device according to one embodiment of the present invention, wherein warm air from the vacuum exhaust is used to nebulise medication and/or humidify air and deliver it to the user's nostrils. Many users requiring respiratory support often require medication to be delivered to them in nebulized form. In one embodiment, as illustrated in FIG. 3, the warm exhaust air from the vacuum pump 22 is conveyed by pipe 52 to the user's nostrils directly, as illustrated in the figure, or alternatively via a nasal mask or helmet. En-route to the nose, the pipe 52 narrows while passing over medication and/or humidifier tank 54. Air passing through this narrowing, draws up the liquid medication and/or water via venturi effect and mixes with it—creating a fine mist of the medication and/or humidified air, which travels via the pipe 52 to the user's nostrils. This can be regulated by the regulator 56 on the pipe 52 and used as and when required. The rest of the time, the vacuum pump 22 exhausts out to the atmosphere via outlet 58.

In the foregoing specification, specific embodiments of the present invention have been described. However, one of ordinary skill in the art will appreciate that various modifications and changes can be made without departing from the spirit and scope of the present invention as set forth in the various embodiments discussed above and the claims that follow. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements as described herein.

We claim:

1. A respiratory device comprising:
   a flexible shell that is configured to enclose front and side parts of a user's chest and/or abdomen, wherein the flexible shell is configured to enclose less than 2 liters of dead space between the flexible shell and the user's chest and/or abdomen;
   an assembly located on and directly attached to the flexible shell, wherein the assembly comprises:
      one or more vacuum chambers communicating with the dead space enclosed by the flexible shell when secured to the user via at least one first opening through a fast acting valve;
      one or more compressed air chambers communicating with the dead space enclosed by the flexible shell when secured to the user via at least one second opening through the fast acting valve;
      a vacuum generating source connected to the one or more vacuum chambers;
      a compressed air generating source connected to the one or more compressed air chambers;
      one or more sensors and one or more electronic control units that are configured to operate the respiratory device, wherein the fast acting valve is configured to operate within microseconds of the user's initiation of inhalation effort or within microseconds of command from the one or more electronic control units, and shuttle between the one or more vacuum chambers and the one or more compressed air chambers for providing instantaneous pre-stored vacuum or compressed air to the dead space to synchronize with the user's breath;
      one or more battery and/or electrical connection to an external power source attached to the one or more electronic control units to power the respiratory device, the respiratory device requiring less than 20 watts of power, and
   a sealing mechanism that is configured to seal the flexible shell to the user's chest and/or abdomen;
   wherein the respiratory device weighs less than 1.5 kilograms.

2. The respiratory device of claim 1, wherein: the vacuum generating source and the compressed air generating source of the assembly comprise (i) a vacuum pump and a compressor, or (ii) a compressor that generates both compressed air and vacuum via venturi effect principle; and
   wherein the assembly is a detachable separate unit from the flexible shell, and attachable to other shells of different sizes.

3. The respiratory device of claim 1, wherein:
   the vacuum generating source and the compressed air generating source of the assembly are external to the flexible shell and comprise (i) an external vacuum pump and a compressor, (ii) a compressor that generates both vacuum and compressed air via venturi effect principle, (iii) vacuum and compressed air outlets of hospital pipelines, or (iv) a compressed air outlet of the hospital pipelines that generates both vacuum and compressed air via venturi effect principle, wherein
   said vacuum generating source and the compressed air generating source communicate with the one or more vacuum chambers and the one or more compressed air chambers by means of high pressure pipes of small bore with diameter of less than 1 centimeter, and wherein the high pressure pipes withstand pressures of 4 bar and 75% vacuum.

4. The respiratory device of claim 1, wherein the respiratory device is configured to auto-start ventilating to the user on fastening a shell fastening mechanism.

5. The respiratory device of claim 1, further comprising pipes that are configured to supply warm air from the respiratory device to the user's nose, to nebulize medicine and/or to humidify air for delivering to the user's nose via nasal pipes, a mask or a helmet.

6. The respiratory device of claim 1, wherein the flexible shell is adjustable to minimize dead space between the one or more vacuum chambers and the user's chest and/or abdomen.

7. The respiratory device of claim 1, wherein at least one of the flexible shell, the one or more vacuum chambers and the one or more compressed air chambers are made utilizing thin-walled, structurally supported elements or thin shells that are well stiffened with narrowly spaced ribs or lattice structures.

8. The respiratory device of claim 1, wherein:
   the one or more electronic control units are connectable to an external programming device comprising a mobile phone or a computing device to customize settings per user via wired or wireless network; or
   the one or more electronic control units are connected to an input device comprising a keypad, a display unit or a touchscreen, the input device attached to the flexible shell to program various settings comprising respiratory rate, rhythm, pressures, and tidal volume onto the respiratory device as desired.

9. The respiratory device of claim 1, wherein the respiratory device is programmed to provide resistance training to the user's respiratory muscles, to improve strength of respiratory muscles, and/or to improve the respiratory rate, rhythm, and volume of the user.

10. The respiratory device of claim 1, wherein the respiratory device is utilized to generate and provide positive pressure ventilation to the user via nasal pipes, a mask, a helmet or an endotracheal tube.

11. The respiratory device of claim 1, wherein the sealing mechanism comprises a seal comprising soft foamed cells covered with an outer skin for preventing air from within the seal from communicating with the atmosphere while at the same time allowing movement of air within the seal.

* * * * *